United States Patent [19]

Sato et al.

[11] 4,066,678

[45] Jan. 3, 1978

[54] 3-TRIHYDROXYGERMYL PROPIONIC ACID AND ITS SALTS AND A PROCESS FOR THE PRODUCTION THEREOF

[75] Inventors: Ryuichi Sato, Oizumimachi; Akira Ishikawa, Tokyo; Yukihito Ishida, Tokyo; Hiroshi Sato, Tokyo; Setsuo Tomisawa, Tokyo; Shigeshi Toyoshima, Tokyo; Shiro Ikegami, Funabashi, all of Japan

[73] Assignee: Ryuichi Sato, Oizumimachi, Japan

[21] Appl. No.: 697,568

[22] Filed: June 18, 1976

[30] Foreign Application Priority Data

Oct. 23, 1975 Belgium .................................. 161181

[51] Int. Cl.$^2$ .............................................. C07F 7/30
[52] U.S. Cl. .................................. 260/429 R; 424/287
[58] Field of Search ...................... 260/429 R; 424/287

[56] References Cited

U.S. PATENT DOCUMENTS

| 3,689,516 | 9/1972 | Asai et al. | 260/429 R |
| 3,812,167 | 5/1974 | Pahk | 260/429 R |

OTHER PUBLICATIONS

J. Organometal. Chem. v. 89, pp. 43–47 (1975).

*Primary Examiner*—Helen M. S. Sneed

*Attorney, Agent, or Firm*—Hubbell, Cohen, Stiefel & Gross

[57] ABSTRACT

Novel pharmacologically important organic germanium compounds (3-hydroxygermyl propionic acid salts) represented by the formula

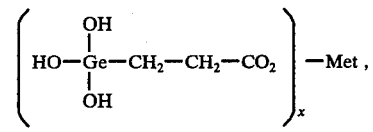

wherein Met is a monovalent cation selected from the group consisting of Na, K, $NH_4$, and $NH_2(CH_3)_2$, or divalent cation selected from the group consisting of Ca and Mg, and wherein $x$ is 1 when Met is a monovalent cation and $x$ is 2 when Met is a divalent cation.

These compounds possess valuable therapeutic properties for treating such physiological abnormality as psychiatric and neurological disorders, metabolic disorder, cardivascular disorder, disorder of digestive organs, skin disease, allergic disease, Kidney dysfunction, hepatic dysfunction, obstetric and pediatric diseases, etc., and the process for preparing thereof.

5 Claims, No Drawings

3-TRIHYDROXYGERMYL PROPIONIC ACID AND ITS SALTS AND A PROCESS FOR THE PRODUCTION THEREOF

DETAILED DESCRIPTION OF THE INVENTION

The present invention relates to novel pharmacologically important organic germanium compounds possessing valuable therapeutic properties, a method for their preparation and their use.

It is, therefore, an object of the invention to provide a novel compound 3-hydroxygermyl propionic acid and its salts represented by the formula I

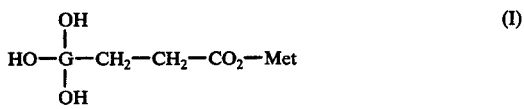

wherein Met is a monovalent cation selected from the group consisting of Na, K, $NH_4$, and $NH_2(CH_3)_2$, or a divalent cation selected from the group consisting of Ca and Mg, and wherein $x$ is 1 when Met is a monovalent cation and $x$ is 2 when Met is a divalent cation.

It is also another object of the invention to provide a process for preparing the compounds represented by the above formula I and salts thereof, which comprises reacting trichlorogermanium with acrylic acid to result 3-trichlorogermyl propionic acid, hydrolyzing the produced germyl propionic acid with a caustic alkali solution to result 3-germylpropionic acid oxide of the formula III $$(Ge-CH_2-CH_2-CO_2H)_{2n}O_{3n} \quad (III)$$

wherein $n$ represents 1, 2, 3 . . . , and reacting the obtained oxide with a hydroxide of the metal Met wherein Met is as defined above, to form an objective compound of the formula I.

An outline of the synthetic route of the title compounds of the formula I is shown in Scheme 1.

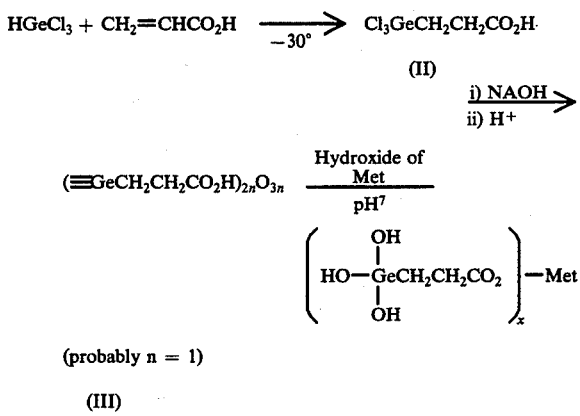

Scheme 1

The addition of trichlorogermane to acrylic acid proceeded readily at −30° to give the corresponding adduct in a high yield. Alkaline hydrolysis of the adduct followed by acidification yielded 3-germylpropionic acid oxide, whose structure could not be characterized completely because of low solubility in usual organic solvents. However, considering the results of elemental analysis and titrimetric method, it seems reasonable that the oxide may be indicated by the general formula of $(\equiv GeCH_2CH_2CO_2H)_{2n}O_{3n}$ where $n=1, 2, 3$ . . . The solubilities in water of the oxides prepared by different procedure are variable. The product derived from hydrolysis of 3-trichlorogermylpropionic acid with water was sparingly soluble in water, while the oxide prepared by the present procedure resulted in relatively high solubility. This suggests that the oxide derived from alkaline hydrolysis may be consisted of the low grade of polymer, namely $n=1$ in the general formula indicated above.

Neutralization of the oxide with various bases, such as sodium hydroxide, potassium hydroxide, ammonium hydroxide, dimethylamine, calcium hydroxide, and magnesium hydroxide, followed by evaporation gave the corresponding salts quantitatively. Elemental analysis supports monomeric structures to salts, but such structure as trihydroxygermyl group trends to have polymeric forms in an acidic medium and usually sensitive to pH of a solution. When the salts are dissolved in water, the solution is in neutral region, so that probably they will give trihydroxygermyl structure.

Thus 3-trihydroxygermylpropionic acid and its salts, sodium salt, potassium salt, dimethylammonium salt, ammonium salt, calcium salt and magnesium salts were synthesized.

The compounds of the invention having the foregoing Formula I are characterized by important pharmacological activity, indicative of their use in counteracting undermentioned physiological abnormalities, as follows:

1. Psychiatric and neurological disorders

Epilepsy, depression, schizophrenia, asthenopia, migrain and peripheral neuritis.

2. Metabolic disorders

Improvement of lipid metabolism, improvement of hypercholestraemia and anti-diabetic effect.

3. Cardiovascular System

Hypertension, enhancement of cardiac activity, antihemorrhagic effect, vascular stability, improvement of peripheral circulation.

4. Digestive Organs

Improvement of gastric, duodenal, or color ulcers. Effect on constipation.

5. Skin Diseases

Psoriasis vulgaris, Acne vulgaris.

6. Allergic Diseases

Bronchial asthma, drug eruption and urticaria.

7. Kidney Function

Diuretic effect. Effect on nephrosis.

8. Treatment of Hepatic Dysfunction

Acute and chronic hepatitis, liver atrophia, liver cirrhosis, fat liver and liver carcinoma.

9. Obstetric and pediatric diseases

Treatment of neutritional disorders during pregnancy and lactation.

Treatment of development disorders in infants and retinopathy of prematurity.

Treatment of actonic vomiting.

10. Preventive effect on long term administration of drugs

11. General fatigue, malaise and asthenia

These compounds are administered by any of oral-, intravenous-, subcutaneous-, intramuscular-, and intrarectal-administrative routes.

These compounds also can be applied on skin in a form of ointment and its modifications in which any of these compounds is contained. Dosage of an organic germanium compound is 1mg/kg/day – 20mg/kg/day in oral route, intravenous-, intramuscular- and subcutaneous- ones, and in both of intrarectal use and an ointment, the preparations containing 0.5–3.0% of an organic germanium compound are made.

The fundamental research concerning the therapeutic effect of 3-hydroxygermyl propionic sodium salt (hereinafter this may be represented by NaOGe as the abbreviation) has been performed and the following results have been obtained:

A. Acute Toxicities of the compounds according to the invention are shown in Table 1, as under:

Table 1.

| Acute Toxicities of NaOGe according to the Invention | | | |
|---|---|---|---|
| Animals | Administrated Route | Sex | $LD_{50}$ |
| Rats (Wistar strain) | per os | Male | over 10g/kg |
|  | per os | Female | over 10g/kg |
| Mice (ICR strain) | per os | Male | over 10g/kg |
|  | per os | Female | over 10g/kg |

B. Therapeutic Effect of NaOGe

1. Effect of NaOGe on Hypertension in Rats

To investigate the effect of NaOGe on hypertension, 100mg/kg/day of sodium salt of OGe had been administered to spontaneously hypertensive rats (SHR strain) and estimated the change of blood pressure.

The experimental results are shown in Table 2.

Table 2.

| Effect of NaOGe on Spontaneously Hypertensive Rats | | | | |
|---|---|---|---|---|
| | | Blood Pressure (mm Hg) | | |
| Rat. No. | Sex | before | 20 days later | 25 days later |
| The Control Group | | | | |
| 1 | M | 190 | 180 | 192 |
| 2 | M | 210 | 220 | 200 |
| 3 | M | 180 | 186 | 178 |
| 4 | M | 187 | 193 | 195 |
| 5 | M | 192 | 190 | 190 |
| 6 | M | 190 | 187 | 195 |
| The Treated Group | | | | |
| 7 | M | 190 | 185 | 145 |
| 8 | M | 190 | 188 | 190 |
| 9 | M | 170 | 130 | 145 |
| 10 | M | 195 | 160 | 155 |
| 11 | M | 188 | 145 | 145 |
| 12 | M | 200 | 210 | 170 |
| 13 | M | 170 | 145 | 150 |
| 14 | M | 180 | 145 | 145 |
| 15 | M | 200 | 155 | 145 |
| 16 | M | 195 | 145 | 120 |

Other salts of organic germanium compound such as magnesium salt, calcium salt, etc., showed similar effects.

From the above experimental results, it may be indicated that OGe is highly effective on hypertension in rats and the effect appears gradually.

2. Effect of OGe and ECG in Clinical Trial

As described in the above section, OGe possesses the effect on hypertension in spontaneously hypertensive rats, and so Dr. Y. Ishida, of our research group investigated the effect on OGe on ECG of human being with heart disease. Among many salts of s-hydroxygermyl-propionic acid, sodium salt thereof has been used in all the following clinical and experimental evaluations as representative organic germanic compound. NaOGe was administered orally and each dose was 75-mg-body.

3. Effect of NaOGe on essential Hypertension in Human Being

Dr. A. Ishikawa, of our research group, has investigated the effect of NaOGe on essential hypertension in human being. The adminstration of 40–150 mg/body of NaOGe was divided orally in two or three doses. The duration of drug administration was at the least 1 month, at the most 12 months. The following results are obtained:

| The Criteria of Effect of NaOGe on Essential Hypertension | |
|---|---|
| Subjective findings | Results |
| recovery of lassitude | 25/(29)* |
| loss of fatigue symptoms | 21/(28) |
| improvements of head ache | 19/(27) |
| improvement of shoulder stiffness | 18/(26) |
| disappearance of palpitation | 7/(10) |
| recovery and increase of appetite | 20/(32) |
| improvement in activity | 18/(32) |
| disappearance of insomnia | 14/(20) |
| sedative action | 16/(20) |
| improvement of the subjective vision | 21/(24) |

*Numbers showing good response / total numbers

The duration of drug administration was at the least 1 month, at the most 12 months. The following results are obtained:

| The Criteria of Effect of NaOGe on Diabetes Mellitus | |
|---|---|
| Subjective findings | Results |
| recovery of lassitude | 6/11 |
| loss of fatigue symptoms | 5/11 |
| improvement of head ache | 2/(3) |
| improvement of shoulder stiffness disappearance of palpitation | 2/(3) |
| recovery and increase of appetite | 6/(11) |
| improvement in activity | 8/(11) |
| disappearance of insomnia | 7/(11) |
| sedative action | 8/(11) |
| improvement of the subjective vision | 9/(11) |
| normalization of the systemic blood pressure | 3/(4) |
| normalization of cranial blood pressure | 2/(4) |
| improvement of manifestations of the optic fundi | 9/(11) |
| prevention of hemorrhage in the optic fungi | 10/(11) |
| increase of the objective vision | 7/(11) |
| improvement of lipids in blood | 6/(10) |
| discontinuation of the weight increase | 1/(4) |
| improvement of ECG | 5/(11) |
| increase of urine volume in a day | 2/(4) |
| decrease of urine sugar | 3/(5) |

*Numbers showing good response / total numbers

From the above findings, it may be said that NaOGe is effective on Diabetes Mellitus.

| The Criteria of Effect | |
|---|---|
| Objective findings | Hypertension |
| normalization of the systemic blood pressure | 32/(37) |
| normalization of cranial blood pressure | 31/(37) |
| improvement of manifestations of the optic fundi | 17/(37) |
| prevention of hemorrhage in the optic fungi | 15/(16) |
| increase of the objective vision | 18/(24) |
| improvement of lipids in blood | 30/(35) |
| discontinuation of the weight increase | 8/(17) |

-continued

| The Criteria of Effect | |
|---|---|
| Objective findings | Hypertension |
| improvement of ECG | 18/(30) |
| increase of urine volume in a day | 4/(7) |

From the above findings, it may be said that NaOGe can be considered effective in the treatment and the prevention of essential hypertension.

3-b. Effect of NaOGe on Diabetes Mellitus in Human Being

Dr. A. Ishikawa of our research group has investigated the effect of NaOGe on Diabetes Millitus in human being. The administration of 40–150 mg/kg body of NaOGe was divided orally in two or three doses.

4. Effect of NaOGe on Amyloidosis Development in Mice

From the above results, it was presumed that OGe might act not only hypertension but some of metabolic changes related to aging. Thus, the influence of NaOGe on the development of amyloidosis in mice was tested. The ICR strain mice had been treated with oral administration of NaOGe for 22 months. After that, all mice were sacrificed and the development of amyloidosis in several important organs was investigated.

The experimental results are shown in Table 3. As can be seen in Table 3, 300mg/kg/day of NaOGe completely inhibited the development of amyloidosis, and even by using 30mg/kg/day of NaOGe a clear prevention of the development was observed.

Table 3.

| Effect of NaOGe on Development of Amyloidosis in Mice | | |
|---|---|---|
| Groups | Numbers of Used Mice | Numbers of Mice Showing Amyloidosis |
| The Control | 14 | 12 |
| 30mg/kg/day of NaOGe group | 6 | 3 |
| 300mg/kg/day of NaOGe group | 12 | 0 |
| 3000mg/kg/day of NaOGe group | 14 | 0 |

5. Effect of NaOGe on Ascites Hepatoma in Rats

Dr. H. Sato, of our research group, investigated the antitumor effect of NaOGe by using several strains of ascites hepatoma in rats. For this investigation, the following ten strains of hepatoma were used: AH13, AH130, AH272, AH44, AH66F, AH7974, AH41C, AH60C and AH109A. $10^7$ cells of each strain tumor were inoculated intravenously into the Doryu rats, 72 hours later, 100mg/kg/day of OGe was administered for 10 days.

No significant effect could be found on AH13, AH130, AH272, AH66F, AH41C and AH109A, but in AH44 and AH66 200% increase of life span was found in the group treated with NaOGe and about the half of the treated rats showed a complete cure, while all rats of the control died. NaOGe, however, does not possess direct cytocidal action. These findings suggest that OGe may be one of new types of anti-tumor chemotherapeutic drugs.

6. Effect of NaOGe on Teratogenic Action of Cadmium Chloride in Golden Hamster

Prof. S. Tomizawa investigated the effect of NaOGe on teratogenic action of cadmium chloride. Cadmium chloride injected intravenously (2.0mg/kg) on the 8th day of gestation to golden hamster produces cleft palate, exencepalia, harelips and open-eye lid.

Malformation produced by cadmium chloride is prevented completely by simultaneous intravenous injection of NaOGe (40.0mg/kg) as shown in Table 4.

Table 4.

| Influence of NaOGe on Teratogenic Action of Cadmium Chloride | | | | |
|---|---|---|---|---|
| Compounds and dose (mg/kg) | | | Living | Resorbed |
| Cadmium chloride | NaOGe | Malformation (%) | fetuses (%) | embryos (%) |
| 2.0 | | 25.5 | 4.9 | 51.0 |
| 2.0 | 2.0 | 25.0 | 5.6 | 37.3 |
| 2.0 | 4.0 | 11.4 | 7.0 | 22.2 |
| 2.0 | 10.0 | 1.8 | 11.0 | 15.4 |
| 2.0 | 20.0 | 2.6 | 7.6 | 25.5 |
| 2.0 | 40.0 | 0 | 7.6 | 11.6 |

7. Clinical Use of Sodium salt of 3-hydroxygermylpropionic Acid a. Epilepsy

A large amount therapy, 100–500mg/body/day in a dosis, is performed. After the start of therapy, the interval of convulsion appearance becomes gradually longer, and the grade of convulsion becomes lighter and more many patients did not show any symptom when the oral administration of the drug is continued. In encephaloelectrogram (EEG), the inhibition of slow burst is not observed, but the loss of epilepsy specific spike is found. The effect of this drug is different from any other anti-epileptic drugs in the following points; (1) complete lack of drowsiness (2) the improvement of learning — and working — ability is observed. In these points, the patients are humanly matured.

b. Depression.

The oral administration of about 100mg/body/day brings the improvement of depressive status. In moderate depression, about at the 8th day after drug administration, the improvement is observed. As the drug does not give any drowsiness, a different point from any other anti-depression drug, the daily life of a patient is not disturbed. The initiation of autonomy is clearly observed after drug administration.

c. Schizophrenia

The oral administration of 200mg/body/day ~ 300mg/body/day is necessary. In this dosis, the disappearance of hullucination is accelerated and the self-recognization that he is suffering from the disease is clearly found rather early after drug administration. The working ability is observed and the remarkable development of this ability is shown after he becomes one of the members of society. Patients do not refuse drug administration.

d. Loss of Autonomic Nervous System Function

The objective and functional abnormality of various organs controlled by autonomic nervous system are not found after drug administration. The oral administration of 75mg/body/day shows the effect on many patients showing resistance against any other drugs.

e. Migrain

The administration of 75mg/body/day of the drug is effective on migraine. The drug shows the effect on the symptoms caused by brain-anemia.

f. Peripheral Neuritis

Many patients, who have been suffering from the symptoms of peripheral neuritis for a long time and have not showed any cure even by using many other drugs, become to enjoy normal daily life without serious pain by the administration of 100mg/body/day.

g. Acceleration of Heart Function

Patients showing the pattern of blood-loss ECG symptom show the improvement of ECG pattern after the administration of 75mg/body/day ~ 150mg/body/day which brings the increase of blood-stream. The stabilizing effect of blood-vessels of the drug is found from the effect on the eye ground symptoms, and more the subcutaneous bleeding of legs and hands of old people is inhibited by this drug-administration.

h. Improvement of Peripheral Circulation

The drug protects the appearance of cold exanthema. In a patient showing peripheral circulation deficiency, the single administration of 50 mg/body/day shows the increase of peripheral circulating blood amount. This is observed by plethysmography.

i. Digestive System

The drug administration brings the loss of subjective symptoms and the cure of ulcers. The effect is found clearly by X-ray examination. The effect is higher than any other therapy. The drug shows the modification of movement of stomach and intestine, and so it is effective on constipation.

j. Allergic Diseases

When 75mg/body/day of the drug is given to the patients suffering from asthma bronchitis and chronic exanthema, the following effects are obtained; (1) the decrease of the frequency of symptom-appearance. (2) the interval of symptom appearance becomes longer. (3) The decrease of adrenal cartex hormone or stop of the hormone is obtained by using the drug. From 6 months to 1 year after the drug administration, many patients show a condition looking like a complete cure. In patients suffering from drug allergy, the drug is given with an allergenic drug, but any drug allergic reaction is not observed.

k. Kidney Function

The diuretic effect is observed after the drug administration, and the appearance of proteiureia is inhibited by this drug.

l. Therapy of Dysfunction Liver

The acceleration of the spontaneous cure of both acute and chronic hepatitis is observed by the drug administration. In patients receiving 100mg/body/day of the drug, the improvement of alkali phosphatase, SGOT, SGPT, ASAC and α-GPT and abnormal fraction of serum-protein was observed.

l-i. Liver Cirrhose

The patients receiving the drug administration of 100mg/body/day ~ 200mg/body/day show the beginning of the loss of ascites, and the acceleration of the recovery of liver function, and stopped the progress of liver dysfunction.

l-ii. Fat Liver

By the drug administration, the similar effect to that in liver cirrhose is obtained.

l-iii. Hepatoma

By the drug administration, the increase of life span is obtained.

m. The Effect in Obstetrics

The drug is particularly-effective on various symptoms including morning sickness caused by pregnancy. The administration of 100mg/body/day ~ 200mg/body/day of the drug is effective one some serious patients who are for an indication of artificial pregnance stopping due to terribly serious pregnance-symptoms.

The drug administration (100~200mg/body/day) to infants showing the decrease of body weight brings the increase and the administration of 20 - 50 mg/body/day is effective on actonic vomiting and autointoxication of infants.

n. Protective Effect of Drug Administration for Long Periods

The long-term administration of tranquilizers and anti-tuberculosis drugs is more easy due to the decrease of side effects by the organic germanium compounds when the drug (50mg/body/day) is administered with the others.

c. General Fatigue, Malaise and Asthenia

The drug administration of 75mg/body/day brings the loss of the symptoms of general fatigue, malaise and asthenia, and the increase of the drug dose to 75mg/body/day shows early the disappearance of the symptoms due to neurosis.

p. Skin Diseases

In Psoriasis Vulgaris, about 60% of patients shows cure by the drug administration of 30~40mg/body/day for 4~5 months and 70% of patients suffering from acne vulgaris show the cure after the drug administration of 30~40mg/body/day for 2 months.

The following examples illustrate the preparative procedures described hereinabove.

EXAMPLE 1.

3-Trichlorogermylpropionic Acid

To a magnetically stirred solution of 18 g (0.1 mole) of trichlorogermane in 30 ml of anhydrous ether was added dropwise with a solution of 7.2g (0.1 mole) of acrylic acid in 20 ml of ether at −30°. Then, the mixture was allowed to stand at room temperature for 2 hrs. Evaporation of the solvent left a solid, which was recrystallized from n-hexane to give 22.5 g (89.3% yield) of white needles, mp 84°~85°. Lit. (V. F. Mironov, E. M. Berliner, and T. K. Gar, *Zh. Obshch. Khim.*, 37, 962 (1967) reports mp 83°~85° for this compound.

3-Germylpropionic acid oxide having the general formula of $(GeCH_2CH_2CO_2H)_{2n}O_{3n}$ where $n = 1, 2, 3$ 3-Trichlorogermylpropionic acid (25.2 g, 0.1 mole) was added portionwise to a stirred 10% sodium hydroxide solution (120 ml) under ice-cooling. The clear solution obtained was continued to stir for additional 30 min and then pH was adjusted to 1.0~2.0 by adding 10% hydrochloric acid or 10% sulfuric acid. White crystals precipitated from the solution were assembled by filtration, dried at 100° under reduced pressure. There was obtained 15.5 g of white needles, mp 300°.

Anal. Calcd for $(\equiv GeCH_2CH_2CO_2H)_{2n}O_{3n}$: C, 21.24; H, 2.97. Found: C, 21.29; H, 2.95.

Numerical value of $n$ could not be determined because of its poor solubility to organic solvents and poor volatility.

EXAMPLE 2

Preparation of the salts of 3-trichlorogermyl propionic acid

1. Sodium 3-trihydroxygermylpropionate

To a suspended solution of 17 g of 3-germylpropionic acid oxide in 34 ml of water was added portionwise 4 g (0.1 mole) of sodium hydroxide under stirring. The oxide dissolved gradually in water with adding sodium hydroxide and the solution became clear by addition of total amounts of the alkali. The reaction mixture (pH=7) was filtered and concentrated under reduced pressure until obtaining a sirup. An addition of 50 ml of ethanol and then scratching by a spatula made a sirup solidified. A solid was collected by filtration, washed with ethanol and dried in a dessicator under reduced pressure. There was obtained 21.4 g (98% yield) of a hydroscopic white powder, mp 300°.

Anal. Calcd for $C_3H_7O_5GeNa$: C, 16.48; H, 3.20. Found: C, 16.35; H, 3.33.

2. Potassium 3-trihydroxygermylpropionate

The potassium salt was prepared in the same procedure as that of the sodium salt using an equimolar amount of potassium hydroxide. Mp was more than 300°.

Anal. Calcd for $C_3H_7O_5GeK$: C, 15.35; H, 3.01. Found: C, 15.20; H, 3.16.

3. Ammonium 3-trihydroxygermylpropionate

The ammonium salt was prepared in the similar procedure to that of the sodium salt using an equimolar amount of conc. ammonium hydroxide solution. The salt was hydroscopic and did not melt even at 300°. A satisfactory analysis was not obtained because of hydroscopic property.

4. Dimethylammonium 3-trihydroxygermylpropionate

The salt was prepared in the similar manner to that of the sodium salt using an equimolar amount of 40% aqueous dimethylamine solution. The salt was extremely hydroscopic and did not melt even at 300°. Because of extremely hygroscopic property, the result of elemental analysis was not satisfactory.

5. Calcium 3-trihydroxygermylpropionate

The calcium salt was prepared in the same procedure as that of the sodium salt using an equimolar amount of calcium hydroxide. The salt did not melt at 300°.

Anal. Calcd for $C_6H_{14}O_{10}Ge_2Ga$: C, 16.70; H, 3.27. Found: C, 16.55; H, 3.35.

6. Magnesium 3-trihydroxygermylpropionate

The magnesium salt was also prepared according to the procedure for the sodium salt using an equimolar amount of magnesium hydroxide. The salt was not melt even at 300°.

Anal. Calcd for $C_6H_{14}O_{10}Ge_2Mg$: C, 17.33; H, 3.39. Found: C, 17.16, H, 3.51.

What is claimed is:

1. A compound of the formula

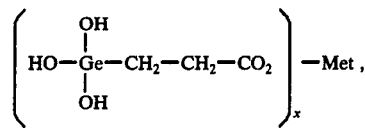

wherein Met is a monovalent cation selected from the group consisting of Na, K, $NH_4$, and $NH_2(CH_3)_2$, or a divalent cation selected from the group consisting of Ca and Mg, and wherein $x$ is 1 when Met is a monovalent cation and $x$ is 2 when Met is a divalent cation.

2. The compound of claim 1 wherein Met is Na and $x$ is 1.

3. The compound of claim 1 wherein Met is Mg and $x$ is 2.

4. The compound of claim 1 wherein Met is Ca and $x$ is 2.

5. A process for preparing the compound of claim 1, which process comprises reacting trichlorogermanium with acrylic acid to thereby obtain 3-trichlorogermyl propionic acid of the formula

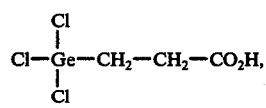

hydrolyzing said acid with caustic alkali solution followed by acidification to thereby obtain 3-germylpropionic acid oxide of the formula

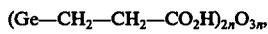

wherein $n = 1$, 2 or 3, and reacting said oxide with a hydroxide of the metal Met, wherein Met is the cation Na, K, $NH_4$, $NH_2(CH_3)_2$, Ca, or Mg, to thereby form the compound of claim 6.

* * * * *

UNITED STATES PATENT OFFICE
CERTIFICATE OF CORRECTION

Patent No. 4,066,678  Dated January 3, 1978

Inventor(s) Ryuichi Sato, Akira Ishikawa, Yukihito Ishida, Hiroshi Sato, Setsuo Tomisawa, Shigeshi Toyoshima, and Shiro Ikegami It is certified that error appears in the above-identified patent and that said Letters Patent are hereby corrected as shown below:

Column 1, lines 14-19, formula (I) should read:

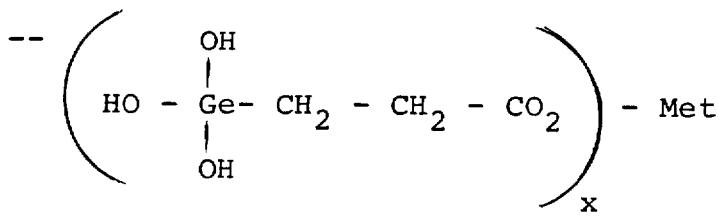

Signed and Sealed this

Twenty-sixth Day of September 1978

[SEAL]

Attest:

RUTH C. MASON
Attesting Officer

DONALD W. BANNER
Commissioner of Patents and Trademarks